(12) United States Patent
Levine et al.

(10) Patent No.: US 8,722,628 B2
(45) Date of Patent: May 13, 2014

(54) AUTOPHAGY-INDUCING PEPTIDE

(71) Applicant: Baylor College of Medicine, Houston, TX (US)

(72) Inventors: Beth C. Levine, Dallas, TX (US); Sanae Shoji-Kawata, Dallas, TX (US); Olivier Lichtarge, Dallas, TX (US); Angela D. Wilkins, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/076,150

(22) Filed: Nov. 8, 2013

(65) Prior Publication Data

US 2014/0066382 A1 Mar. 6, 2014

Related U.S. Application Data

(63) Continuation of application No. PCT/US2013/022350, filed on Jan. 20, 2013.

(60) Provisional application No. 61/597,741, filed on Feb. 11, 2012.

(51) Int. Cl.
*C07K 14/47* (2006.01)
*C07K 14/005* (2006.01)

(52) U.S. Cl.
CPC ............ *C07K 14/4747* (2013.01); *C07K 14/005* (2013.01)
USPC ........... 514/18.9; 530/324; 530/317; 436/501

(58) Field of Classification Search
None
See application file for complete search history.

(56) References Cited

PUBLICATIONS

PCT/US13/22350; International Search Report and Written Opinion.

*Primary Examiner* — Karlheinz R Skowronek
*Assistant Examiner* — Schuyler Milton
(74) *Attorney, Agent, or Firm* — Richard Aron Osman

(57) ABSTRACT

An autophagy-inducing compound comprises an autophagy-inducing peptide comprising beclin-1 residues 269-283 and a heterologous moiety that promotes therapeutic stability or delivery of the compound. The compound may be used to induce autophagy and in assays with beclin-1 binding partners.

18 Claims, No Drawings

AUTOPHAGY-INDUCING PEPTIDE

Applicants claim priority to U.S. Ser. No. 61/597,741, filed: Feb. 11, 2012 and is a continuation of PCT/US13/22350 filed: Jan. 20, 2013.

This invention was made with government support under Grant Number U54A1057156 awarded by the National Institutes of Health (NIH). The government has certain rights in the invention.

INTRODUCTION

The molecular cascade that regulates and executes autophagy has been the subject of numerous comprehensive reviews[1-4] The identification of signals that regulate autophagy and genes that execute autophagy has facilitated detection and manipulation of the autophagy pathway[5]. Phosphatidylethanolamine (PE) conjugation of yeast Atg8 or mammalian LC3 results in a nonsoluble form of Atg8 (Atg8-PE) or LC3 (LC3-II) that stably associates with the autophagosomal membrane. Consequently, autophagy can be detected biochemically (by assessing the generation of Atg8-PE or LC3-II) or microscopically (e.g. by observing the localization pattern of fluorescently tagged Atg8 or LC3).

Our laboratory discovered one of the core essential autophagy genes, beclin 1[6]. Beclin 1 is the mammalian ortholog of yeast Atg6/Vps30[7]. It interacts with the class III phosphatidylinositol 3-kinase (PI3K), Vps34, and is involved in the first step of autophagosome formation[8], the nucleation of the isolation membrane (also known as phagophore) at the endoplasmic reticulum (a process called autophagic vesicle nucleation). Gene knockout/knockdown studies indicate a conserved requirement for ATG6/beclin 1 in autophagy in plants, slime molds, nematodes, fruit flies, mice, and human cells[9]. Decreases in Beclin 1 expression and/or function have been linked to increased susceptibility to cancer, Alzheimer's disease, Huntington's disease, and desmin-related cardiomyopathy; alterations in microbial pathogenesis; defects in apoptotic corpse clearance and development; and aging[9].

Beclin 1 encodes a 450 amino acid protein with a central coiled coil domain. Within its N' terminus, it contains a BH3-only domain, which mediates binding to anti-apoptotic molecules such as Bcl-2 and Bcl -xL[10]. The most highly conserved region, referred to as the evolutionarily conserved domain (ECD), spans from amino acids 244-337, which is important for its interaction with Vps34[10]. Besides Vp34 and Bcl-2 family proteins, Beclin 1 has numerous other binding partners, including Atg14 (another core autophagy protein), UVRAG (a protein that functions in autophagosomal maturation), Rubicon (a negative regulator of the Beclin 1/Vps34 complex), and Ambra1 (a positive regulator of the Beclin 1/Vps34 complex)[9]. In addition, Beclin 1 has been reported to interact with certain receptors and immune signaling adaptor proteins, including the inositol 1, 4, 5-triphosphate receptor (IP3R), the estrogen receptor, MyD88 and TRIF, and nPIST, as well as certain viral virulence proteins such as HSV-1 ICP34, KSHV vBcl-2, HIV-1 Nef, and influenza M2[9]. Overexpression of Beclin 1 is sufficient to induce autophagy[11], and our laboratory has shown that two oncogenic growth signaling molecules activated in human cancers, including the epidermal growth factor receptor and Akt, both interact with Beclin 1 and inhibit its autophagy function.

SUMMARY OF THE INVENTION

The invention provides methods and compositions for inducing autophagy.

In one aspect the invention provides an autophagy-inducing compound or composition comprising (a) an autophagy-inducing peptide comprising Beclin 1 residues 269-283 immediately flanked on each terminus by no more than twelve naturally-flanking Beclin 1 residues, wherein up to six of said residues 269-283 may be substituted, and (b) a first heterologous moiety, e.g. that promotes therapeutic stability or delivery of the compound.

Active such compounds have been developed with a variety of alternative structures and formulations; in various particular embodiments, such as wherein:
- the peptide is N-terminally flanked with T-N and C-terminally flanked by T;
- the peptide comprises at least one of F270, F274 and W277;
- the peptide comprises at least one substitution, particularly of H275E, S279D or Q281 E;
- the peptide is N-terminally joined to the first moiety, and C-terminally joined to a second heterologous moiety;
- the peptide is joined to the first moiety through a linker or spacer;
- the first moiety comprises a transduction domain, including: protein-derived (e.g. tat, smac, pen, pVEC, bPrPp, PIs1, VP22, M918, pep-3), chimeric (e.g. TP, TP10, MPGΔ), and synthetic (e.g. MAP, Pep-1, oligo-Arg) cell-penetrating peptides;
- the first moiety comprises a homing peptide, such as RGD-4C, NGR, CREKA, LyP-1, F3, SMS, IF7 or H2009.1;
- the first moiety comprises a stabilizing agent, such as a PEG, oligo-N-methoxyethylglycine (NMEG), albumin, an albumin-binding protein, or an immunoglobulin Fc domain;
- the peptide comprises one or more D-amino acids, L-β-homo amino acids, D-β-homo amino acids, or N-methylated amino acids;
- the peptide is cyclized;
- the peptide is acetylated, acylated, formylated, amidated, phosphorylated, sulfated or glycosylated;
- the compound comprises an N-terminal acetyl, formyl, myristoyl, palmitoyl, carboxyl or 2-furosyl group, and/or a C-terminal hydroxyl, amide, ester or thioester group;
- the compound comprises an affinity tag or detectable label; and/or
- the peptide is N-terminally joined to the first moiety, and C-terminally joined to a second heterologous moiety comprising a detectable label, such as a fluorescent label.

Particular embodiments include all combinations and subcombinations of particular embodiments, such as wherein:
- the peptide is N-terminally flanked with T-N and C-terminally flanked by T, the first moiety is a tat protein transduction domain linked to the peptide through a diglicine linker; and
- the peptide is N-terminally flanked with T-N and C-terminally flanked by T, the first moiety is a tetrameric integrin α(v)β(6)-binding peptide known as H2009.1, linked to the peptide through a maleimide—PEG(3) linker.

In another aspect the invention provides a method of inducing autophagy, comprising administering to a person in need thereof an effective amount of a subject compound.

The invention also provides methods and compositions for identifying modulators of Beclin -1-GAPR-1 interaction.

In one aspect the invention provides a composition comprising predetermined amounts of (a) the compound of claim 1, Beclin 1, or a GAPR-1-binding Beclin 1 peptide, and (b) GAPR-1, or a GAPR-1-binding Beclin 1 peptide.

In another aspect the invention provides a method of identifying modulators of Beclin-1-GAPR-1 interaction, the method comprising steps: (a) combining a subject composition with an agent under conditions wherein but for the presence of agent, the Beclin 1 or GAPR-1-binding Beclin 1 peptide engages the GAPR-1 or GAPR-1-binding Beclin 1 peptide in control interaction; and (b) detecting a test interaction between the Beclin 1 or GAPR-1-binding Beclin 1 peptide and the GAPR-1 or GAPR-1-binding Beclin 1 peptide, wherein a difference between the control and test interaction identifies the agent as modulator of Beclin-1-GAPR-1 interaction.

DESCRIPTION OF PARTICULAR EMBODIMENTS OF THE INVENTION

In one aspect the invention provides an autophagy-inducing compound or composition comprising (a) an autophagy-inducing peptide comprising Beclin 1 residues 269-283 immediately flanked on each terminus by no more than 12 (or 6, 3, 2, 1 or 0) naturally-flanking Beclin 1 residues, wherein up to six (or 3, 2, 1 or 0) of said residues 269-283 may be substituted, and (b) a first heterologous moiety, e.g. that promotes therapeutic stability or delivery of the compound.

The autophagy-inducing peptide comprises Beclin 1 residues 269-283 (VFNATFHIWHSGQFG; SEQ ID NO:01) immediately flanked on each terminus by no more than 12 (or 6, 3, 2, 1 or 0) naturally-flanking Beclin 1 residues, wherein up to six (or 3, 2, 1 or 0) of said residues 269-283 may be substituted. As exemplified herein, peptide and compound activity are tolerant to a variety of additional moieties, flanking residues, and substitutions within the defined boundaries. For example, in some embodiments the peptide is N-terminally flanked with T-N and C-terminally flanked by T (TNVFNATFHIWHSGQFGT; SEQ ID NO:02). In other embodiments the peptide comprises at least one (or 2 or 3) of substitutions: H275E, S279D and Q281E (e.g. VFNATFEIWHDGEFG; SEQ ID NO:03). In other embodiments the peptide comprises at least one (or 2 or 3) of F270, F274 and W277.

Peptide and compound activity are also tolerant to backbone modification and replacement, side-chain modifications, and N- and C-terminal modifications, all conventional in the art of peptide chemistry.

Chemical modifications of the peptide bonds may be used to provide increased metabolic stability against enzyme-mediated hydrolysis; for example, peptide bond replacements (peptide surrogates), such as trifluoroethylamines, can provide metabolically more stable and biologically active peptidomimetics.

Modifications to constrain the peptide backbone include, for example, cyclic peptides/peptidomimetics which can exhibit enhanced metabolic stability against exopeptidases due to protected C- and N-terminal ends. Suitable techniques for cyclization include Cys-Cys disulfide bridges, peptide macrolactam, peptide thioether, parallel and anti-parallel cyclic dimers, etc.

Other suitable modifications include acetylation, acylation (e.g. lipopeptides), formylation, amidation, phosphorylation (on Ser, Thr and/or Tyr), etc. which can be used to improve peptide bioavailability and/or activity, glycosylation, sulfonation, incorporation of chelators (e.g. DOTA, DPTA), etc. PEGylation can be used to increase peptide solubility, bioavailability, in vivo stability and/or decrease immunogenicity, and includes a variety of different PEGs: HiPEG, branched and forked PEGs, releasable PEGs; heterobifunctional PEG (with endgroup N-Hydroxysuccinimide (NHS) esters, maleimide, vinyl sulfone, pyridyl disulfide, amines, and carboxylic acids), etc.

Suitable terminal modifications include N-terminal acetyl, formyl, myristoyl, palmitoyl, carboxyl and 2-furosyl, and C-terminal hydroxyl, amide, ester and thioester groups, which can make the peptide more closely mimic the charge state in the native protein, and/or make it more stable to degradation from exopeptidases.

The peptides may also contain atypical or unnatural amino acids, including D-amino acids, L-β-homo amino acids, D-β-homo amino acids, N-methylated amino acids, etc.

The compound comprises a first moiety, heterologous to (not naturally flanking) the Beclin 1 peptide, typically one that promotes therapeutic stability or delivery, and optionally, a same or different second moiety, preferably also heterologous to the Beclin 1 peptide. In a particular embodiment, the peptide is N-terminally joined to the first moiety, and C-terminally joined to the second moiety.

A wide variety of such moieties may be employed, such as affinity tags, transduction domains, homing or targeting moieties, labels, or other functional groups, such as to improve bioavailability and/or activity, and/or provide additional properties.

One useful class of such moieties include transduction domains which facilitate cellular penetrance or uptake, such as protein-derived (e.g. tat, smac, pen, pVEC, bPrPp, PIs1, VP22, M918, pep-3); chimeric (e.g. TP, TP10, MPGΔ) or synthetic (e.g. MAP, Pep-1, Oligo Arg) cell-penetrating peptides; see, e.g. "Peptides as Drugs: Discovery and Development", Ed. Bernd Groner, 2009 WILEY-VCH Verlag GmbH & Co, KGaA, Weinheim, esp. Chap 7: "The Internalization Mechanisms and Bioactivity of the Cell-Penetrating Peptides", Mats Hansen, Elo Eriste, and Ulo Langel, pp. 125-144.

Another class are homing biomolecules, such as RGD-4C (CCDCRGDCFC; SEQ ID NO:04), NGR (CCNGRC; SEQ ID NO:05), CREKA, LyP-1 (CGNKRTRGC; SEQ ID NO:06), F3, SMS (SMSIARL; SEQ ID NO:07), IF7, and H2009.1 (Li et al. Bioorg Med Chem. 2011 Sep 15;19(18):5480-9), particularly cancer cell homing or targeting biomolecules, wherein suitable examples are known in the art, e.g. e.g. Homing peptides as targeted delivery vehicles, Pirjo Laakkonen and Kirsi Vuorinen, Integr. Biol., 2010, 2, 326-337; Mapping of Vascular ZIP Codes by Phage Display, Teesalu T, Sugahara K N, Ruoslahti E., Methods Enzymol. 2012; 503:35-56.

Other useful classes of such moieties include stabilizing agents, such as PEG, oligo-N-methoxyethylglycine (NMEG), albumin, an albumin-binding protein, or an immunoglobulin Fc domain; affinity tags, such as immuno-tags, biotin, lectins, chelators, etc.; labels, such as optical tags (e.g. Au particles, nanodots), chelated lanthanides, fluorescent dyes (e.g. FITC, FAM, rhodamines), FRET acceptor/donors, etc.

The moieties, tags and functional groups may be coupled to the peptide through linkers or spacers known in the art, such as polyglycine, ε-aminocaproic, etc.

The compound and/or peptide can also be presented as latent or activatable forms, such as a prodrug, wherein the active peptide is metabolically liberated; for example, release of the linear peptide from cyclic prodrugs prepared with an acyloxyalkoxy promoiety (prodrug 1) or a 3-(2'-hydroxy-4', 6'-dimethylphenyl)-3,3-dimethyl propionic acid promoiety (prodrug 2) of the compound).

Particular embodiments include all combinations of particular embodiments, as though each had be separately set forth; for example, wherein the peptide is N-terminally flanked with T-N and C-terminally flanked by T, the first moiety is a tat protein transduction domain linked to the peptide through a diglycine linker; and wherein the peptide is N-terminally flanked with T-N and C-terminally flanked by T, the first moiety is a tetrameric integrin α(v)β(6)-binding peptide known as H2009.1, linked to the peptide through a maleimide—PEG(3) linker.

In another aspect the invention provides a method of inducing autophagy, comprising administering to a person in need thereof an effective amount of a subject compound or composition. Applications broadly encompass persons in need of enhanced autophagy, and include diseases and pathologies where the upregulation of autophagy is therapeutically beneficial, including infection with intracellular pathogens, neurodegenerative diseases, cancers, cardiomyopathy, and aging.

Autophagy can be detected directly, indirectly or inferentially by conventional assays, such as disclosed and/or exemplified herein, including biochemically (by assessing the generation of Atg8-PE or LC3-II or the degradation of p62) or microscopically (e.g. by observing the localization pattern of fluorescently tagged Atg8 or LC3).

The invention also provides methods and compositions for identifying modulators of Beclin-1-GAPR-1 interaction.

In one aspect the invention provides a composition comprising predetermined amounts of (a) the compound of claim 1, Beclin 1, or a GAPR-1-binding Beclin 1 peptide, and (b) GAPR-1, or a GAPR-1-binding Beclin 1 peptide.

In another aspect the invention provides a method of identifying modulators of Beclin-1-GAPR-1 interaction, the method comprising steps: (a) combining a subject composition with an agent under conditions wherein but for the presence of agent, the Beclin 1 or GAPR-1-binding Beclin 1 peptide engages the GAPR-1 or GAPR-1-binding Beclin 1 peptide in control interaction; and (b) detecting a test interaction between the Beclin 1 or GAPR-1-binding Beclin 1 peptide and the GAPR-1 or GAPR-1-binding Beclin 1 peptide, wherein a difference between the control and test interaction identifies the agent as modulator of Beclin-1-GAPR-1 interaction. This assay may be practice in a variety of formats, including fluorescent polarization, pull-down, solid-phase binding, etc.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

A. Tat-Beclin 1 Peptide is a Potent Inducer of Autophagy in vitro

The HIV-1 viral protein Nef has been shown to interact with the autophagy protein, Beclin 1[12]. To map the domain of Beclin 1 that is essential for its interaction with HIV-1 Nef, we co-transfected different flag epitope-tagged Beclin 1 deletion mutants (amino acids 1-377, 141-450 and 257-450) with a C' terminal HA epitope-tagged Nef. All three flag-Beclin 1 deletion mutants co-immunoprecipitated with Nef-HA, suggesting that the common overlapping region, amino acids 244-377 of Beclin 1, referred to as the evolutionarily conserved domain (ECD), may be involved in binding to HIV-1 Nef.

To test this hypothesis, we constructed several Beclin 1 mutants containing different deletions within the ECD. Co-immunoprecipitation experiments showed that amino acids 267-299 of Beclin 1 are essential for Beclin 1 to bind to Nef. We constructed two additional deletion mutants to further map which amino acids of Beclin 1 within the region of 267-299 are required for binding to HIV-1 Nef. Compared to a Beclin 1 deletion mutant lacking aa 285-299, a deletion mutant lacking aa 267-284 showed weaker binding to HIV-1 Nef. This indicates that amino acids 267-284 of Beclin 1 in the ECD are crucial for Beclin 1's interaction with HIV-1 Nef.

We next investigated whether amino acids 267-284 of Beclin 1 are required for the autophagy function of Beclin 1. To do this, we used MCF-7 cells that express low levels of endogenous Beclin 1 and are deficient in starvation-induced autophagy in the absence of exogenous Beclin 1 expression[7, 11]. MCF-7 cells were co-transfected with a plasmid encoding a green-labeled marker of autophagosomes, GFP-LC3[13], and either full-length Flag-Beclin 1 or Flag-Beclin 1 containing a deletion of amino acids 267-284. The number of autophagosomes (GFP-LC3 dots) was quantitated after culture in normal or starvation media. In normal media, autophagy levels were similar in cells transfected with empty vector, and plasmids expressing WT Flag-Beclin 1 and Flag-Beclin1Δ267-284. Starvation increased autophagy in MCF-7 cells transfected with WT Flag-Beclin 1, but not in cells transfected with empty vector or Flag-Beclin1Δ267-284, indicating that amino acids 267-284 of Beclin 1 are crucial for the autophagy function of Beclin 1.

We next asked whether amino acids 267-284 of Beclin 1 are sufficient to induce autophagy. To evaluate this, we designed a cell-permeable peptide composed of the HIV-1 Tat protein transduction domain (PTD), a diglycine linker, and 18 amino acids derived from the region of Beclin 1 spanning amino acids 267-284. Three substitutions were made in this region, including H275E, S279D and Q281E, to enhance the hydrophilicity and optimize the solubility of the peptide. To confirm that these substitutions have no effect on Beclin 1 expression or Beclin 1/Nef interactions, we constructed a plasmid expressing the mutant Flag-Beclin 1 H267E/S279D/Q281E. Flag-Beclin 1 H267E/S279D/Q281E co-immunoprecipitated with Nef-2HA as efficiently as did WT Flag-Beclin 1, indicating that the substitution, H267E, S279D and Q281E in Beclin 1 does not change its binding to HIV-1 Nef. Further studies confirmed that this Beclin 1 activity is tolerant to additional substitutions.

Therefore, we synthesized a 31 amino acid length peptide, named Tat-Beclin 1 (T-B) composed of the Tat protein transduction domain, a diglycine linker and 18 amino acids from amino acids 267-284 of Beclin that includes the substitutions, H267E, S279D and Q281E. As a control peptide, the 18 amino acids of Beclin 1 in Tat-Beclin 1 were randomly shuffled to generate a peptide referred to as Tat-Scrambled (T-S). A circular dichroism spectrum of Tat-Beclin 1 and Tat-Scrambled exhibited very similar patterns, indicating that these two peptides have similar three-dimensional structures and that Tat-Scrambled is an appropriate control peptide for the Tat-Beclin 1 peptide.

Next, to investigate whether Tat-Beclin 1 peptide induces autophagy, we analyzed protein levels of p62 and LC3[5]. p62 is selectively degraded by the autophagy machinery and its protein levels reflect the amount of autophagic flux (i.e. a complete autophagy response). Lipidated LC3 (LC3-II), but not unlipidated LC3 (LC34), binds to autophagosomes and LC3 lipidation correlates with autophagosome formation. Western blot analysis revealed that p62 protein levels were decreased and LC3-II protein levels were increased after Tat- Beclin 1 peptide treatment in multiple cell lines including HeLa, COS-7, MEFs, A549, HBEC30-KT, THP1, and HCC827 cells. The precise dose required to induce autophagy, as measured by p62 degradation and LC3-II conversion varied somewhat in different cell types. In contrast to the results with Tat-Beclin 1, levels of p62 and LC3-II expression did not change in cells treated with Tat-Scrambled control peptide at any dose tested.

We confirmed the autophagy-inducing effects of the Tat-Beclin 1 peptide using four additional assays. First, we assessed whether Tat-Beclin 1 increases autophagosome numbers in HeLa cells stably expressing GFP-LC3[14]. Cells treated with Tat-Beclin 1 had a 27-fold increase in numbers of GFP-LC3 dots (autophagosomes) as compared to cells treated with the Tat-Scrambled control peptide; the magnitude of this induction is higher than that seen with the most potent known physiological inducer of autophagy, starvation. Second, we performed electron microscopy to confirm the presence of autophagic structures in HeLa cells treated with Tat-Beclin 1. Numerous autophagosomes and autolysosomes were observed in cells treated with Tat-Beclin 1, whereas very few autophagic structures were observed in cells treated with Tat-Scrambled. Third, we confirmed that Tat-Beclin 1 peptide treatment increases autophagic flux by measuring levels of p62 and LC3-II in the presence and absence of Bafilomycin A1, a vacuolar $H^+$-ATPase inhibitor that inhibits autophagic degradation by blocking autophagosomal/lysosomal fusion. As noted above, in the absence of Bafilomycin A1, Tat-Beclin 1 increased levels of LC3-II and decreased levels of p62 in HeLa and COS-7 cells. Bafilomycin A1 resulted in a further marked increase in LC3-II levels and a mild increase in p62 protein levels in HeLa and COS-7 cells treated with Tat-Beclin 1 as compared to those observed in Tat-Beclin 1-treated cells without Bafilomycin A1. This indicates that Tat-Beclin 1 peptide treatment enhances autophagic flux. Fourth, to further analyze the autophagic flux induced by the Tat-Beclin 1 peptide, we assessed bulk degradation of long-lived proteins by measuring the release of TCA-soluble [$^3$H] leucine from cells. Long-lived protein degradation was significantly increased in Tat Beclin 1 as compared to Tat-Scrambled-treated cells. This increase was partially blocked by 3-methyladenine (3-MA), an inhibitor of phosphatidylinositol-3-kinases that blocks autophagosome formation[15]. Together, these results indicate that the Tat-Beclin 1 peptide induces autophagosome formation and enhances autophagic degradation through lysosomes.

We investigated whether Tat-Beclin 1-mediated autophagy involves a canonical autophagy pathway by using siRNA to knockdown two essential autophagy genes, ATG7 and beclin 1. HeLa cells transfected with A TG7- and beclin 1-targeting siRNA had decreased protein expression of Atg7 and Beclin 1, respectively and significantly decreased numbers of autophagosomes. These data demonstrate that the canonical autophagy, involving both members of the Class III/PI3K complex (i.e. Beclin 1) and the protein conjugation systems (i.e. Atg7) is involved in Tat-Beclin 1 peptide mediated-autophagy.

B. Mutation Analyses of the Tat-Beclin 1 Peptide

We next performed additional mutation analyses of the Tat-Beclin 1 peptide to determine the minimal biologically active region and identify potentially essential residues in the 18-mer sequence linked to the Tat protein transduction domain. Mutation of the tryptophan residue at amino acid 277 of Beclin 1 to an isoleucine decreased the activity of Tat-Beclin 1, as measured by Western blot analyses of p62 levels and LC3-II conversion, and mutation of phenylalanaine at position 270 to serine or phenylalanine at position 274 to serine blocked Tat-Beclin 1 peptide-mediated autophagy induction. However, a peptide with substitutions at F274 and W277 retained significant activity.

We then constructed a series of truncation mutants lacking amino acids at either the N' terminus and/or the C' terminus of the 18-mer sequence of Beclin 1 in the peptide, Tat-Beclin 1. Deletion of the C' terminal one amino acid ($\Delta$C-1), the N' terminal one amino acid ($\Delta$N-1), the N' terminal two amino acids ($\Delta$N-2), the N' terminal three amino acids (AN-3), or both the N' terminal two amino acids and the C' terminal amino acid ($\Delta$N-2/$\Delta$C-1) resulted in peptides that had similar activity as the full-length Tat-Beclin 1 peptide, or even greater activity (in the case of $\Delta$N-2), as measured by the magnitude of decrease in p62 levels and increase in LC3-II conversion. Peptides containing deletion of the C' terminal two amino acids ($\Delta$C-2) or the N' terminal four amino acids ($\Delta$N-4) were less active than Tat-Beclin 1. We synthesized a peptide lacking the N' terminal three amino acids and C' terminal amino acid ($\Delta$N-3/$\Delta$C-1) but this peptide was not soluble in PBS. Based on these mutation analyses, we conclude that Tat-$\Delta$N-2/$\Delta$C-1 is the shortest active form of the Tat-Beclin 1 peptide, and the Tat-$\Delta$AN2 may be the most active form of those we have tested.

C. The Tat-Beclin 1 Peptide Induces Autophagy in Multiple Tissues in vivo

To investigate whether Tat-Beclin 1 peptide induces autophagy in mice, we used mice that transgenically express, GFP-LC3, a marker protein for autophagosomes[16]. We injected Tat-Beclin 1 or Tat-Scrambled peptides i.p. into 6-8 week-old mice at a dose of 20 mg/kg, and at 6 h post-injection, harvested two tissues, lung and skeletal muscle (vastus lateralis). Significantly greater numbers of autophagosomes were observed in muscle tissue and in pulmonary macrophages of mice treated with Tat-Beclin 1 as compared to with Tat-Scrambled. In 5 day-old suckling mice, we assessed autophagy induction by measuring levels of p62 protein expression in the brains of mice treated with Tat-Scrambled control, Tat-Beclin 1 peptide, or a retro-inverso D-amino acid version of Tat-Beclin 1. We found that were was a significant decrease in p62 levels in the brains of mice treated with either the L- or D-form of the Tat-Beclin 1 peptide as compared to mice treated with the Tat-Scrambled peptide control. Based on multiple repeat experiments, in aggregate, the D-form of Tat-Beclin 1 appears to be more active in inducing autophagy in the brain. We also compared the levels of autophagy induction in skeletal muscle, cardiac muscle and exocrine pancreas after treatment with the L- and D-forms of Tat-Beclin 1. We found that in all three of these tissues, the D-form of Tat-Beclin 1 treatment resulted in significantly higher levels of autophagosomes than the L-form of Tat-Beclin 1 treatment, and further studies confirm that this activity is tolerant to additional substitutions in the Beclin 1 peptide.

D. The Tat-Beclin 1 Peptide Decreases the Accumulation of Aggregates in Cells Expressing Mutant Human Huntingtin Protein The induction of autophagy leads to the clearance of aggregate-prone mutant huntingtin (Htt) protein that causes Huntington's disease (HD)[17, 18]. To investigate whether Tat-Beclin 1-mediated autophagy decrease Htt aggregates and levels of Htt protein, we treated HeLa/Htt103Q cells, a HeLa cell line expressing exonl of htt that encodes a polyQ expansion of 103 residues (Htt103Q)[19], with Tat-Beclin 1 peptide. The cell line expresses doxycycline (dox)-repressible Htt103Q fused to CFP which makes it possible to evaluate the clearance of Htt by fluorescence microscopyl[19]. Consistent with previous reports indicating that autophagy does not clear large protein aggregates, Tat-Beclin 1 peptide treatment had no effect on the number of large (>1 μm) Htt103Q aggregates. However, Tat-Beclin 1 treatment (for 4 h per day for two days) decreased the number of small (<1 μm) Htt103Q aggregates as efficiently as treatment with doxycycline (100 ng/ml) which inhibits the expression of Htt103Q. These findings were confirmed biochemically using a filter trap assay to separate large protein aggregates, small protein aggregates and soluble protein. Similar to our microscopic analyses, Tat-Beclin 1 peptide decreased the amount of Htt103Q protein in small aggregates to a similar degree as doxycycline suppression of Htt103Q protein synthesis. Moreover, Tat-Beclin 1 peptide also resulted in a marked decrease in the levels of expression of soluble Htt103Q protein. These findings indicate that the Tat-Beclin 1 peptide can clear the pre-aggregated and small aggregated form of mutant Htt protein, and provide a rationale for preclinical testing of this agent in the treatment of Huntington's and other neurodegenerative diseases.

E. The Tat-Beclin 1 Peptide Has Activity Against Sindbis virus, West Nile virus, Chikungunya virus, mouse-adapted Ebola virus, L. monocytogenes and HIV1

Previously, we showed that overexpression of Beclin 1 decreases Sindbis virus replication in mouse brain[6]. More recently, we showed that mice lacking the autophagy gene, Atg5, in neurons are more susceptible to lethal Sindbis virus infection of the central nervous system[14], and our collaborator has shown that mice with a hypomorphic allele of the Atg16L1 autophagy gene are more susceptible to lethal chikungunya virus infection[20]. In addition, other studies have shown that genetic knockout or knockdown of beclin 1 and other autophagy genes increases the replication of a variety of viruses, including tobacco mosaic virus in plants[21] and vesicular stomatitis virus in *drosophila*[22]. Together, these studies indicate an important role for autophagy in the control of many different viruses.

Therefore, we investigated the hypothesis that the Tat-Beclin 1 peptide would inhibit viral replication using HeLa cells infected with two alphaviruses, Sindbis virus and chikungunya virus, and one flavivirus, West Nile virus. For all experiments, we used a dose of the Tat-Beclin 1 peptide (30 μm for 4 h) that had no cellular toxicity, as measured by trypan blue exclusion and MTT assays. We infected HeLa cells with Sindbis virus, chikungunya virus, or West Nile virus at a multiplicity of infection of 0.1 plaque-forming unit per cell, treated the cells with Tat-Scrambled or Tat-Beclin 1 peptide four h after infection for a period of 4 h, and then measured viral titers at 18 h post-infection (for Sindbis virus) or 24 h post-infection (for chikungunya virus and West Nile virus). We found a significant decrease (≥2 log) in viral titers in cells infected with all three viruses that were treated with Tat-Beclin 1 peptide as compared to Tat-Scrambled control. To determine whether Tat-Beclin 1 peptide treatment could be effective in reducing viral replication if administered at a later time point after infection (mimicking the situation that would occur if this peptide were to be used as a therapeutic in patients with viral infections), we initiated daily peptide treatment of chikungunya virus infection, beginning 24 h after infection. This resulted in a significant decrease in viral titers at 48 and 72 h p.i., which was associated with significantly less virus-induced cytopathic effects. These data indicate that Tat-Beclin 1 peptide treatment initiated after the onset of infection has antiviral activity against several different enveloped-positive strand RNA viruses.

Our collaborator, Robert Davey, at UTMB, also tested the antiviral activity of the Tat-Beclin 1 peptide in Vero cells and HeLa cells infected with mouse-adapted Ebola virus. In these experiments, cells were pre-treated with Tat-Scrambled control or Tat-Beclin 1 peptide for 1 h, cells were infected at an MOI of 0.1 pfu, and the percentage of virus-infected cells was determined at 24 h post-infection. The results showed that the Tat-Beclin 1 peptide resulted in a decrease in mouse-adapted Ebola virus infectivity in both Vero and HeLa cells.

Tat-beclin 1 peptide decreased the intracellular survival of L. monocytogenes in primary murine bone-marrow derived macrophages (BMDMs). We used a strain of L. monocytogenes lacking the autophagy evasion protein, ActA and a dose of the peptide (10 μM for 2 h) that is nontoxic to uninfected BMDMs. This antibacterial effect was decreased in BMDMs derived from Atg5flox/floxLysozymeM-Cre mice that had decreased Atg5 expression and decreased Tat-beclin 1-induced autophagy.

Tat-beclin 1 markedly inhibited HIV-1 replication in primary human MDMs. Using an established pretreatment model (Campbell et al., J Biol Chem 286, 18890-902, 2011; PLoS Pathog 8, e1002689, 2012), we observed a dose-dependent inhibition of HIV p24 antigen release in MDMs cultured in the presence of non-toxic concentrations (0.5, 1, 2.5, and 5 μM) of Tat-beclin 1, with nearly undetectable antigen levels in cells treated daily with 5 μM Tat-beclin 1 peptide. The magnitude of inhibition of HIV-1 replication was similar to that observed with the mTOR inhibitor rapamycin, which also induces autophagy. Tat-beclin 1 peptide-mediated inhibition of HIV-1 replication appeared to occur via the canonical autophagy pathway, as shRNA knockdown of the essential autophagy gene, ATG5, decreased Tat-beclin 1-induced autophagy (as assessed by LC3 lipidation) and completely abrogated the antiviral effects of Tat-beclin 1 treatment without any decrease in cell survival.

F. The Tat-Beclin 1 Peptide Has Antimycobacterial Activity in vitro Against M. tuberculosis in a Human Macrophage Cell Line, THP1 cells.

Several studies have demonstrated that autophagy plays a crucial role in host defense against M. tuberculosis[23, 24, 25], the causative agent of tuberculosis. M. tuberculosis is the most important global pathogen; approximately, one-third of the world's population has tuberculosis, and 2-3 million deaths occur from tuberculosis annually. Better treatments are needed to treat and eradicate tuberculosis.

To evaluate whether the Tat-Beclin 1 peptide may have anti-mycobacterial activity, we infected phorbol ester-differentiated THP-1 cells (a model of human macrophages) with M. tuberculosis. One day after infection, cells were treated with different doses of Tat-Beclin 1 or Tat-Scrambled peptide, and intracellular bacterial growth was measured 6 days later. We found that doses of 10 μm of Tat-Beclin 1 peptide or more resulted in a significant decrease in M. tuberculosis bacterial growth.

G. The Tat-Beclin 1 Peptide has Beneficial Effects on Chikungunya Virus Infection in Mice After determining that the Tat-Beclin 1 peptide inhibits chikungunya virus replication in vitro, we assessed its effects on mortality and viral replication in a mouse neonatal infection model. Chikungunya causes an acute febrile illness, including some fatal cases, and is an emerging pathogen that has become a major problem in Southeast Asia[26]. In addition, it is considered by the National Institute of Allergy and Infectious Diseases to be an agent of potential biothreat. There is currently no specific treatment for chikungunya and no vaccine is available for this disease.

To evaluate the effect of Tat-Beclin 1 chikungunya virus pathogenesis in mice, we infected C57BL6 mice with $10^6$ pfu subcutaneously (s.c.) and treated the mice daily with 15 mg/ml of Tat-Beclin 1 peptide intraperitoneally (i.p) beginning at day 1 post-infection (p.i.) and for 13 days thereafter.

By day 6 after infection, we found that there were significant reductions in viral titers in two muscle groups examined, the vastus lateralis and the soleus. To confirm that autophagy is induced in chikungunya virus-infected muscle, we examined the muscle of GFP-LC3 transgenic mice infected with virus and treated with Tat-Beclin 1 peptide. In virus-infected muscle cells, labeled by immunostaining with an antibody against the chikungunya virus envelope protein E2 antibody, there were significant more GFP-LC3 positive dots in mice treated with Tat-Beclin 1 peptide as compared to mice treated with Tat-Scrambled control peptide Importantly, the antiviral effect in vivo of the Tat-Beclin 1 peptide was associated with a significant reduction in animal lethality. One hundred percent of animals treated with Tat-Scrambled peptide succumbed to lethal disease, as compared to 58% of animals treated with Tat-Beclin 1 peptide.

H. The Tat-Beclin 1 Peptide has Beneficial Effects on West Nile Virus Infection in Mice West Nile virus is an important global emerging pathogen, and since its introduction to North America in 1999, is the most frequent cause of epidemic meningoencephalitis in North America[27]. Although neuroinvasive disease (aseptic meningitis, encephalitis, myelitis) is a rare manifestation of infection (approximately 1% of infected indivudal), the morbity and mortality rates are quite high in those with neurological disease. As with other arboviruses, there is presently no available antiviral treatment. In addition, there is no vaccine available.

To determine whether the Tat-Beclin 1 peptide might exert protective activity against neurological infections caused by arboviruses, we used a model of West Nile virus neurological infection involving direct intracerebral inoculation of the Egypt strain of West Nile virus into neonatal mice[28, 29]. One day after infection, we treated mice with either the L-amino acid form of Tat-Beclin 1 or the D-amino acid form of Tat-Beclin 1. Although the L-amino acid form of Tat-Beclin 1 was capable of inducing protection against chikungunya virus infection, D-amino acid Tat protein transduction domain-linked peptides have increased stability due to resistance to enzymatic cleavage by serum and tissue peptidases and have demonstrated superior intracellular delivery in vivo[30]. Therefore, in view of our use of a CNS infection model in which the peptide needs to be active within the brain, we compared the efficacy of the L-amino acid form and the D-amino acid form of Tat-Beclin 1. Our results demonstrate that the D-amino acid form of Tat-Beclin 1, but not the L-amino acid form of Tat-Beclin 1, resulted in a significant reduction in West Nile virus titers in the brain at day 4 and 6 after infection and a significant delay in virus-induced lethality.

I. The Tat-Beclin 1 Peptide has Anti-Rickettsial Activity in vivo

Rickettsia are a group of vector-borne bacteria that can cause severe human infections, including epidemic typhus and Rocky Mountain spotted fever[31, 32]. Rickettsia are the first intracellular bacterial pathogen for which the cellular pathway of autophagy has been postulated to represent a host defense mechanism[32]. Therefore, in collaboration with Dr. Gustavo Valbuena at UTMB, a specialist in rickettsiosis, we evaluated the effects of Tat-Beclin 1 treatment in a mouse model of Rickettsia conorii infection. We found that Tat-Beclin 1 peptide treatment resulted in a significant reduction in bacterial load in the lung (measured at day 6 after infection) and a trend towards reduction in the liver and brain. These results were obtained with the L-amino acid form of Tat-Beclin 1, and additional studies are now being repeated with the D-amino acid form of Tat-Beclin 1.

J. The Tat-Beclin 1 Peptide Induces Dose-Dependent Cell Death, Including in Chemoresistant Cancer Cells In the studies above, we describe protective effects of autophagy on cells that contain huntingtin aggregates or that are infected with viruses or intracellular bacteria However, high levels of autophagy can induce cell death, which could potentially be useful as a therapeutic for killing cancer cells. Therefore, we examined the ability of the Tat-Beclin 1 to induce cell death.

Using HeLa cells, which are a cervical cancer epithelial cell line, we found that cells undergo a time-dependent increase in cell death after Tat-Beclin 1 treatment, but not after Tat-Scrambled control treatment. There is also a dose-dependent effect. The death caused by Tat-Beclin 1 is autophagic cell death rather than apoptosis or necroapoptosis, as it is not blocked by an inhibitor of apoptosis (z-VAD) or necroapoptosis (Nec-1) but is blocked by an inhibitor of autophagy (3-MA). In addition, it is partially blocked by siRNA against the autophagy genes, ATG7 or beclin 1. To examine whether there is any specificity of the peptide for killing tumorigenic versus non-tumorigenic cells, we compared clonigenic survival of non-tumorigenic immortalized human mammary epithelial cells (HMECs) with tumorigenic MCF7 human breast carcinoma cells. We found that the Tat-Beclin 1 peptide induced a dose-dependent decrease in survival, but MCF7 cells were more sensitive to Tat-Beclin 1 peptide-induced cell death than HMECs. These data indicate that tumorigenic cells may be more sensitive to Tat-Beclin 1 peptide induced cell death.

We have discovered that non-small cell lung carcinoma cell lines with activating mutations in the epidermal growth factor receptor (EGFR) such as HCC827 cells undergo autophagic cell death in response to EGFR tyrosine kinase inhibitor therapy (generic name: Erlotinib; trade name: Tarceva). One of the main problems with Tarceva therapy in patients with this type of lung cancer is that resistance mutations frequently develop; in a lung cancer cell line (H1975 cells) that contains the most common resistance mutation in EGFR, T790M, Tarceva fails to induce autophagy and fails to kill the cells. We therefore asked whether treatment with the Tat-Beclin 1 peptide could overcome this resistance to autophagy induction and cell death. We found that treatment with Tat-Beclin 1 peptide resulted in a marked induction of autophagy in H1975 cells and decrease in clonigenic survival. These findings indicate that the Tat-Beclin 1 peptide may be able to kill cancer cells that are otherwise resistant to chemotherapy-induced autophagic cell death. Additionally, peptides that mediate the intracellular delivery of the Beclin 1 peptide (other than Tat) in a cancer cell-specific manner may be useful for selectively inducing autophagic cell death in tumor cells without inducing cell death in normal cells: our ongoing studies performed in collaboration with Dr. Kathlynn Brown at UT Southwestern use lung cancer cell-specific peptide delivery sequences (e.g. H2009.1) conjugated to the 18 amino acids of Beclin 1 that are contained within Tat-Beclin 1.

K. The Tat-Beclinl Peptide Binds to GAPR-1, a Novel Component of the Autophagy-inducing Beclin 1/Vps34 Complex To investigate how the Tat-Beclin 1 peptide induces autophagy, we performed biochemical analyses to identify binding proteins of the Tat-Beclin 1 peptide. Of note, amino acids 267-284 were not required for known binding partners of the Beclin 1 ECD, such as Vps34, suggesting this region of Beclin 1 is required for its interaction with as-of-yet-unidentified binding partners of Beclin 1. To isolate proteins that bind to Tat-Beclin 1, we used a cell-permeable biotin-conjugated Tat-Beclin 1 peptide, treated HeLa cells for 3 h with the peptide (or a control biotin-conjugated Tat-Scrambled peptide), and mixed lysates with streptavidin beads. Comparing the proteins that bound to biotin-conjugated Tat-Beclin 1 as compared to biotin-conjugated Tat-Scrambled, we observed a specific band in the sample of proteins that bound to biotin-conjugated Tat-Beclin 1 between 15 and 20 kDa. This band was identified by LC-MS/LC analysis as GAPR-1, a protein which has previously been reported to bind to liposomes that contain negatively charged lipids including phosphatidylinositol[33]. We confirmed the interaction between biotin-Tat-Beclin 1 and GAPR-1 by using an anti-GAPR-1 antibody to perform immunoblot analysis of samples prepared by the same method as used for LC-MS/MS analysis. We also examined whether amino acids 267-284 of Beclin 1 (the region contained within the Tat-Beclin 1 peptide is required for the full-length Beclin 1 protein to interact with GAPR-1. Our results indicate that wild-type Beclin 1 co-immunoprecipitates with GAPR-1 but a Beclin 1 deletion mutant lacking amino acids 267-284 does not interact with GAPR-1 above background levels of non-specific binding. Together, these data indicate that amino acids 267-284 of Beclin 1 are both necessary and sufficient for Beclin 1 to interact with GAPR-1.

We evaluated the function of GAPR-1 in autophagy by evaluating the effects of GAPR-1 siRNA on autophagy using an autophagic flux inhibitor. We found that siRNA knockdown of GAPR-1 increased autophagy in both in cells treated with Tat-Scrambled control peptide and in cells treated with Tat-Beclin 1 peptide. These data indicate that GAPR-1 is a novel Beclin 1 interacting protein that functions as a negative regulator of autophagy, and that GAPR-1 and its interaction with Beclin 1 provide a novel targets for autophagy-promoting therapeutic screening and design.

L. Exemplary Alternative Autophagy-Inducing Constructs
1. HIV-1 Tat PTD-diglycine-Beclin 1 residues 267-284
2. HIV-1 Tat PTD-diglycine-Beclin 1 residues 267-284, H275E
3. HIV-1 Tat PTD-diglycine-Beclin 1 residues 267-284, S279D
4. HIV-1 Tat PTD-diglycine-Beclin 1 residues 267-284, Q281E
5. HIV-1 Tat PTD-diglycine-Beclin 1 residues 267-284, H275E, S279D, Q281E
6. HIV-1 Tat PTD-diglycine-Beclin 1 residues 267-284, H275E, S279D, Q281E, V269I, A272G, G283A
7. HIV-1 Tat PTD-diglycine-Beclin 1 residues 267-284, F274 and W277
8. HIV-1 Tat PTD-diglycine-Beclin 1 residues 268-284
9. HIV-1 Tat PTD-diglycine-Beclin 1 residues 267-283
10. HIV-1 Tat PTD-diglycine-Beclin 1 residues 269-284
11. HIV-1 Tat PTD-diglycine-Beclin 1 residues 268-283
12. HIV-1 Tat PTD-diglycine-Beclin 1 residues 269-283
13. HIV-1 Tat PTD-diglycine-Beclin 1 residues 257-283
14. HIV-1 Tat PTD-diglycine-Beclin 1 residues 269-283
15. HIV-1 Tat PTD-diglycine-Beclin 1 residues 257-295
16. H2009.1-maleimide-PEG(3)-Beclin 1 residues 267-284
17. FLAAG-maleimide-PEG(3)-Beclin 1 residues 267-284
18. biotin-maleimide-PEG(3)-Beclin 1 residues 267-284
19. pVec-ε-aminocaproic-PEG(3)-Beclin 1 residues 267-284
20. RGD-4C-ε-aminocaproic-PEG(3)-Beclin 1 residues 267-284
21. maleimide-PEG(3)-Beclin 1 residues 267-284
22. albumin-ε-aminocaproic-PEG(3)-Beclin 1 residues 267-284
23. FITC-Ser-PEG(3)-Beclin 1 residues 267-284-polyHis
24. GFP-PA-Beclin 1 residues 267-284-TAP
25. PEG-Beclin 1 residues 267-284-Cys-AuNP
26. HIV-1 Tat PTD-diglycine-Beclin 1 residues (D) 269-284
27. HIV-1 Tat PTD-diglycine-Beclin 1 residues (D) 269-284
28. HIV-1 Tat PTD-diglycine-Beclin 1 residues 267-284, N-271 N-linked N-acetylglucosamine
29. HIV-1 Tat PTD-diglycine-Beclin 1 residues 267-284, N-271 N-linked N-acetylglucosamine, S279 O-linked N-acetyl-galactosamine
30. HIV-1 Tat PTD-diglycine-Beclin 1 residues (N-methyl) 269-284
31. HIV-1 Tat PTD-diglycine-Beclin 1 residues N-acetyl-269-284-C-amide
32. HIV-1 Tat PTD-Cys-Beclin 1 residues 269-284-Cys (disulfide cyclic)

Abbreviations: H2009.1: tetrameric integrin $\alpha(v)\beta(6)$-binding peptide; PTD: protein transduction domain; PA: α-helices bundle domain of Staphylococcal protein A; GFP: green fluorescent protein; AuNP: gold nanoparticles;

References
1. Levine, B. & Kroemer, G. Autophagy in the pathogenesis of disease. *Cell* 132, 27-42 (2008).
2. Levine, B. & Klionsky, D. J. Development by self-digestion: molecular mechanisms and biological functions of autophagy. *Dev Cell* 6, 463-477 (2004).
3. Klionsky, D. J. Autophagy: from phenomenology to molecular understanding in less than a decade. *Nat Rev Mol Cell Biol* 8, 931-7 (2007).
4. Mizushima, N. & Klionsky, D. J. Protein turnover via autophagy: implications for metabolism. *Annu Rev Nutr* 27, 19-40 (2007).
5. Mizushima, N., Yoshimori, T. & Levine, B. Methods in mammalian autophagy research. *Cell* 140, 313-26 (2010).
6. Liang, X. H. et al. Protection against fatal Sindbis virus encephalitis by Beclin, a novel Bcl-2-interacting protein. *J Virol* 72, 8586-96 (1998).
7. Liang, X. H. et al. Induction of autophagy and inhibition of tumorigenesis by beclin 1. *Nature* 402, 672-6 (1999).
8. Kihara, A., Kabeya, Y., Ohsumi, Y. & Yoshimori, T. Beclin-phosphatidylinositol 3-kinase complex functions at the trans-Golgi network. *EMBO Rep* 2, 330-5 (2001).
9. He, C. & Levine, B. The Beclin 1 interactome. *Curr Opin Cell Biol* 22, 140-9 (2010).
10. Furuya, N., Yu, J., Byfield, M., Pattingre, S. & Levine, B. The evolutionarily conserved domain of Beclin 1 is required for Vps34 binding, autophagy and tumor suppressor function. *Autophagy* 1, 46-52 (2005).
11. Pattingre, S. et al. Bcl-2 antiapoptotic proteins inhibit Beclin 1-dependent autophagy. *Cell* 122, 927-39 (2005).
12. Kyei, G. B. et al. Autophagy pathway intersects with HIV-1 biosynthesis and regulates viral yields in macrophages. *J Cell Biol* 186, 255-68 (2009).
13. Kabeya, Y. et al. LC3, a mammalian homologue of yeast Apg8p, is localized in autophagosome membranes after processing. *Embo J* 19, 5720-8 (2000).
14. Orvedahl, A. O. et al. Autophagy protects against Sindbis virus infection of the central nervous system. *Cell Host & Microbe* 7, 115-127 (2010).
15. Seglen, P. O. & Gordon, P. B. 3-Methyladenine: specific inhibitor of autophagic/lysosomal protein degradation in isolated rat hepatocytes. *Proc Natl Acad Sci U S A* 79, 1889-92 (1982).
16. Mizushima, N., Yamamoto, A., Matsui, M., Yoshimori, T. & Ohsumi, Y. In vivo analysis of autophagy in response to nutrient starvation using transgenic mice expressing a fluorescent autophagosome marker. *Mol Biol Cell* 15, 1101-11 (2004).

17. Ravikumar, B. et al Inhibition of mTOR induces autophagy and reduces toxicity of polyglutamine expansions in fly and mouse models of Huntington disease. *Nat Genet* 36, 585-95 (2004).
18. Mizushima, N., Ohsumi, Y. & Yoshimori, T. Autophagosome formation in mammalian cells. *Cell Struct Funct* 27, 421-9 (2002).
19. Yamamoto, A., Cremona, M. L. & Rothman, J. E. Autophagy-mediated clearance of huntingtin aggregates triggered by the insulin-signaling pathway. *J Cell Biol* 172, 719-31 (2006).
20. Joubert, P. et al. Chikungunya virus-induced autophagy delays apoptosis via the induction of ER stress and generation of reactive oxygen species. *J Exp Med* In revision (2012).
21. Liu, Y. et al. Autophagy regulates programmed cell death during the plant innate immune response. *Cell* 121, 567-77 (2005).
22. Shelly, S., Lukinova, N., Bambina, S., Berman, A. & Cherry, S. Autophagy is an essential component of Drosophila immunity against vesicular stomatitis virus. *Immunity* 30, 588-98 (2009).
23. Levine, B., Mizushima, N. & Virgin, H. W. Autophagy in immunity and inflammation. *Nature* 469, 323-35 (2011).
24. Watson, R., Mazanillo, P. & Cox, J. Delivery of Mycobacterium tuberculosis to autophagy is a major determinant of host defense. *Abstract* Zing Conference on Autophagy, Xcaret, Mexico (2011).
25. Deretic, V. et al. Autophagy in immunity against mycobacterium tuberculosis: a model system to dissect immunological roles of autophagy. *Curr Top Microbiol Immunol* 335, 169-88 (2009).
26. Pulmanausahakul, R., Roytrakul, S., Auewarakul, P. & Smith, D. R. Chikungunya in Southeast Asia: understanding the emergence and finding solutions. *Int J Infect Dis* 15, e671-6 (2011).
27. Debiasi, R. L. West nile virus neuroinvasive disease. *Curr Infect Dis Rep* 13, 350-9 (2011).
28. Eldadah, A. H. & Nathanson, N. Pathogenesis of West Nile Virus encepahlitis in mice and rats. II. Virus multiplication, evolution of immunofluorescence, and development of histological lesions in the brain. *Am J Epidemiol* 86, 776-90 (1967).
29. Eldadah, A. H., Nathanson, N. & Sarsitis, R. Pathogenesis of West Nile Virus encephalitis in mice and rats. 1. Influence of age and species on mortality and infection. *Am J Epidemiol* 86, 765-75 (1967).
30. Mishra, R. et al. Cell-penetrating peptides and peptide nucleic acid-coupled MRI contrast agents: evaluation of cellular delivery and target binding. *Bioconjug Chem* 20, 1860-8 (2009).
31. Walker, D. H. & Ismail, N. Emerging and re-emerging rickettsioses: endothelial cell infection and early disease events. *Nat Rev Microbiol* 6, 375-86 (2008).
32. Walker, D. H., Popov, V. L., Crocquet-Valdes, P. A., Welsh, C. J. & Feng, H. M. Cytokine-induced, nitric oxide-dependent, intracellular antirickettsial activity of mouse endothelial cells. *Lab Invest* 76, 129-38 (1997).
33. Van Galen, J. et al. Binding of GAPR-1 to negatively charged phospholipid membranes: unusual binding characteristics to phosphatidylinositol. *Mol Membr Biol* 27, 81-91 (2010).

---

What is claimed is:

1. An autophagy-inducing compound comprising (a) an autophagy-inducing peptide comprising Beclin 1 residues 269-283 (SEQ ID NO:1) immediately flanked on each terminus by no more than 12 naturally-flanking Beclin 1 residues, wherein up to six of said residues 269-283 may be substituted, and (b) a first heterologous moiety that is heterologous to the peptide.

2. The compound of claim 1, wherein the peptide is N-terminally flanked with T-N and C-terminally flanked by T.

3. The compound of claim 1, wherein the peptide comprises at least one of F270, F274 and W277.

4. The compound of claim 1, wherein the peptide comprises at least one of substitutions: H275E, S279D and Q281E.

5. The compound of claim 1, wherein the peptide is N-terminally joined to the first moiety, and C-terminally joined to a second heterologous moiety.

6. The compound of claim 1, wherein the peptide is joined to the first moiety through a linker.

7. The compound of claim 1, wherein the first moiety comprises a transduction domain.

8. The compound of claim 1, wherein the first moiety comprises homing peptide.

9. The compound of claim 1, wherein the first moiety comprises a serum stabilizing agent.

10. The compound of claim 1, wherein the peptide comprises one or more D-amino acids, L-β-homo amino acids, D-β-homo amino acids, or N-methylated amino acids.

11. The compound of claim 1 wherein the peptide is cyclized.

12. The compound of claim 1 comprising an N-terminal acetyl, formyl, myristoyl, palmitoyl, carboxyl or 2-furosyl group, and/or a C-terminal hydroxyl, amide, ester or thioester group.

13. The compound of claim 1 wherein the peptide is acetylated, acylated, formylated, amidated, phosphorylated, sulfated or glycosylated.

14. The compound of claim 1 comprising an affinity tag or detectable label.

15. The compound of claim 1, wherein the peptide is N-terminally joined to the first moiety, and C-terminally joined to a second heterologous moiety comprising a fluorescent label.

16. The compound of claim 1, wherein the peptide is N-terminally flanked with T-N and C-terminally flanked by T, and the first moiety is a tat protein transduction domain linked to the peptide through a diglycine linker.

17. The compound of claim 1, wherein the peptide is N-terminally flanked with T-N and C-terminally flanked by T, and the first moiety is a tetrameric integrin $\alpha(v)\beta(6)$-binding peptide known as H2009.1, linked to the peptide through a maleimide-PEG(3) linker.

18. A method of inducing autophagy, comprising administering to a person in need thereof an effective amount of a composition of claim 1.

* * * * *

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial sequence
<220> FEATURE:
<223> OTHER INFORMATION: Synthetic

<400> SEQUENCE: 1

Val Phe Asn Ala Thr Phe His Ile Trp His Ser Gly Gln Phe Gly
1               5                   10                  15

<210> SEQ ID NO 2
<211> LENGTH: 18
<212> TYPE: PRT
<213> ORGANISM: Artificial sequence
<220> FEATURE:
<223> OTHER INFORMATION: Synthetic

<400> SEQUENCE: 2

Thr Asn Val Phe Asn Ala Thr Phe His Ile Trp His Ser Gly Gln Phe
1               5                   10                  15

Gly Thr

<210> SEQ ID NO 3
<211> LENGTH: 15
<212> TYPE: PRT
<213> ORGANISM: Artificial sequence
<220> FEATURE:
<223> OTHER INFORMATION: Synthetic
```

```
<400> SEQUENCE: 3

Val Phe Asn Ala Thr Phe Glu Ile Trp His Asp Gly Glu Phe Gly
1               5                   10                  15

<210> SEQ ID NO 4
<211> LENGTH: 10
<212> TYPE: PRT
<213> ORGANISM: Artificial sequence
<220> FEATURE:
<223> OTHER INFORMATION: Synthetic

<400> SEQUENCE: 4

Cys Cys Asp Cys Arg Gly Asp Cys Phe Cys
1               5                   10

<210> SEQ ID NO 5
<211> LENGTH: 6
<212> TYPE: PRT
<213> ORGANISM: Artificial sequence
<220> FEATURE:
<223> OTHER INFORMATION: Synthetic

<400> SEQUENCE: 5

Cys Cys Asn Gly Arg Cys
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic

<400> SEQUENCE: 6

Cys Gly Asn Lys Arg Thr Arg Gly Cys
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic

<400> SEQUENCE: 7

Ser Met Ser Ile Ala Arg Leu
1               5
```